United States Patent [19]

Hunt

[11] Patent Number: 4,823,866
[45] Date of Patent: Apr. 25, 1989

[54] TUBE SUPPORT FOR HEAT EXCHANGER
[75] Inventor: Harold R. Hunt, Bartlesville, Okla.
[73] Assignee: Phillips Petroleum Company, Bartlesville, Okla.
[21] Appl. No.: 118,822
[22] Filed: Nov. 9, 1987
[51] Int. Cl.$^4$ .............................................. F28D 7/00
[52] U.S. Cl. .................................... 165/162; 122/510; 248/68.1
[58] Field of Search ............... 165/162, 169, 172, 178; 122/510, 511, 512; 248/68.1; 29/157.3

[56] References Cited

U.S. PATENT DOCUMENTS

| | | | |
|---|---|---|---|
| 2,573,161 | 10/1951 | Tadewald | 165/153 |
| 3,708,142 | 1/1973 | Small | 248/49 |
| 4,127,165 | 11/1978 | Small | 122/510 |
| 4,136,736 | 1/1979 | Small | 165/162 |
| 4,398,595 | 8/1983 | Small | 165/162 |
| 4,413,394 | 11/1983 | Small | 29/157.3 |
| 4,429,739 | 2/1984 | Gentry et al. | 165/169 |
| 4,490,896 | 1/1985 | Small | 29/157.3 |
| 4,595,161 | 6/1986 | Williams | 165/162 |
| 4,637,455 | 1/1987 | Tordonato | 122/510 |
| 4,670,397 | 6/1987 | Wegner et al. | 435/289 |
| 4,697,637 | 10/1987 | Young | 165/162 |

FOREIGN PATENT DOCUMENTS

| | | | |
|---|---|---|---|
| 1401292 | 4/1965 | France | 165/162 |
| 2430588 | 3/1980 | France | 165/162 |

Primary Examiner—James C. Yeung
Attorney, Agent, or Firm—Williams, Phillips & Umphlett

[57] ABSTRACT

The tubes in a tube bundle through which heat exchange medium flows transversely are supported by rods arranged at a substantial angle with respect to the direction of fluid flow. In a preferred embodiment, tube bundles supported by rods are positioned in a stirred vessel for heat exchange with the fluid in the stirred vessel. In a further preferred embodiment, the stirred vessel is a fermentor for the production of bacteria or yeast.

12 Claims, 5 Drawing Sheets

TUBE SUPPORT FOR HEAT EXCHANGER

In one aspect, the invention relates to an apparatus for supporting a plurality of tubes. In another aspect, the invention relates to a heat exchange apparatus. In still another aspect, the invention relates to heat exchange in a stirred vessel.

BACKGROUND

Heat exchange is required for many chemical conversion reactions, either to remove the heat of reaction or to provide the heat necessary to promote the desired chemical conversion. Tube bundles, i.e., bundles of parallel tubes, are an efficient means to expose a high surface area of heat exchange surface to the reaction fluid. A problem encountered with tube bundles is the need to provide adequate support to the individual tubes so that the tubes retain their structural integrity in the face of strong mixing and vibrating forces as well as thermally induced stresses. Such forces are particularly taxing on the individual tubes of a tubing bundle where the fluid which is passed over the heat exchange surface is directed largely perpendicular to the tube length. There is, therefore, a need to provide adequate means of suporting the individual tubes of a tube bundle which is subjected to high levels of stress during operation, e.g., as in a stirred vessel.

OBJECTS OF THE INVENTION

An object of the present invention is to provide an effective means to support the individual tubes in a bundle of parallel tubes.

Another object of the present invention is to provide a stirred vessel with a highly efficient means for heat exchange.

Another object of the invention is to provide a heat exchange process especially well adapted for use with a stirred vessel.

SUMMARY OF THE INVENTION

In one embodiment of the invention, there is provided an apparatus comprising a plurality of parallel tubes forming a tube bundle having a longitudinal axis. The tubes are arranged in a plurality of parallel tube rows and regular straight lanes are defined through the tube bundle transverse to the direction of the tube rows. A first plurality of lanes is defined through the tube bundle at an angle of $+\theta_1$ with respect to the direction of the tube rows and a second plurality of lanes is defined through the tube bundle at an angle of $-\theta_1$ with respect to the direction of the tube rows. A third plurality of lanes is defined through the tube bundle at an angle of $+\theta_2$ with respect to the direction of the tube rows and a fourth plurality of lanes is defined through the tube bundle at an angle of $-\theta_2$ with respect to the direction of the tube rows. $\theta_1$ ranges from about 10° to about 60°. $\theta_2$ ranges from about 20° to about 80°. $\theta_2$ is greater than $\theta_1$. For such a tube bundle, a support apparatus is formed from a first band or ring and a second band or ring, each of which embraces an outer tube limit of the tube bundle. A first plurality of rods is attached to the first band and extends through the first plurality of lanes. The rods have a sufficiently large diameter to contact the tubes which define the limits of each lane in which rods are positioned. The first plurality of rods comprises sufficient rods attached to the first band so that each tube of the tube bundle is contacted by at least one rod of the first plurality of rods. A second plurality of rods is attached to the second band and extends through the second plurality of lanes. Each rod of the second plurality is of sufficient diameter to contact the tubes defining the limits of each lane in which rods are positioned. The second plurality of rods comprises sufficient rods so that each tube of the tube bundle is contacted by at least one rod of the second plurality of rods. By forming a tube bundle from tubes spread apart so as to form the recited plurality of lanes, rods can be positioned through the first plurality of lanes and the second plurality of lanes to provide the tube bundle with improved ability to withstand transverse fluid flow.

In another embodiment of the invention, there is provided a process for exchanging heat with a stirred fluid in a stirred vessel. The process comprises flowing the fluid through one or more tube bundles each of which is formed from parallel rows of parallel tubes lined up along chords extending across a generally cylindrically portion of the inside sidewall of the vessel. Each of the tube bundles is formed from about 2 to about 20 rows of tubes and the tubes in the adjacent rows are displaced from each other so that the tubes are laid out in a triangular pitch. The individual tubes in each row are provided with radial support by a pair of rod baffles each of which contain sufficient rods so that each tube in the tube bundle is supported on two sides by each rod baffle, together the pair of rod baffles supporting all four sides of each tube so as to provide each tube in the tube bundle with radial support. The open network of the rods provides tube support without unduly restricted fluid flow. Because a high amount of crossflow through the tube bundle, the pressure drop caused by positioning rods in every available lane is not as great as where essentially longitudinal flow of shell side fluid would be present. The additional rods positioned in each baffle allow radial support to be provided with fewer baffles than where each baffle contains a far fewer number of rods than can be accommodated by the bundle at the location of the baffle.

DETAILED DESCRIPTION OF THE INVENTION

Figure 1:
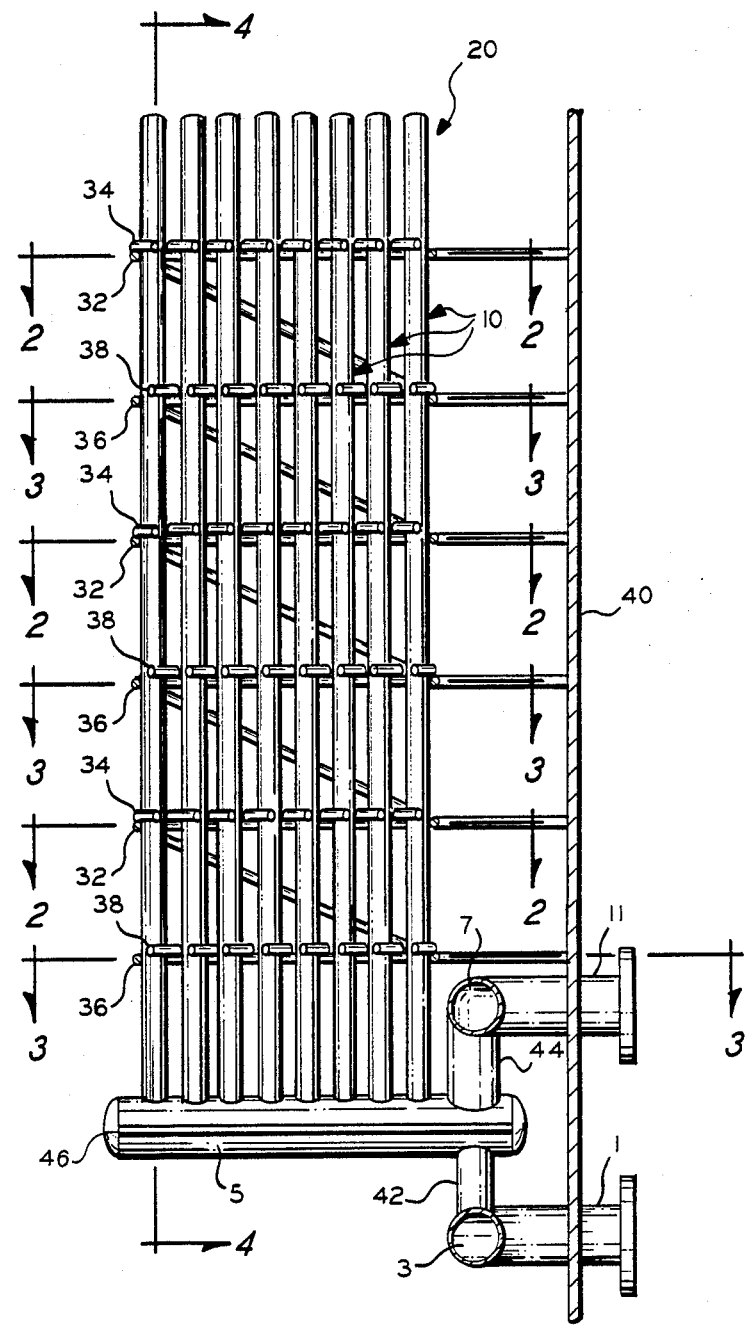
FIG. 1 is a longitudinal sectional view of a tube bundle embodying certain features of the present invention.
Figure 3:
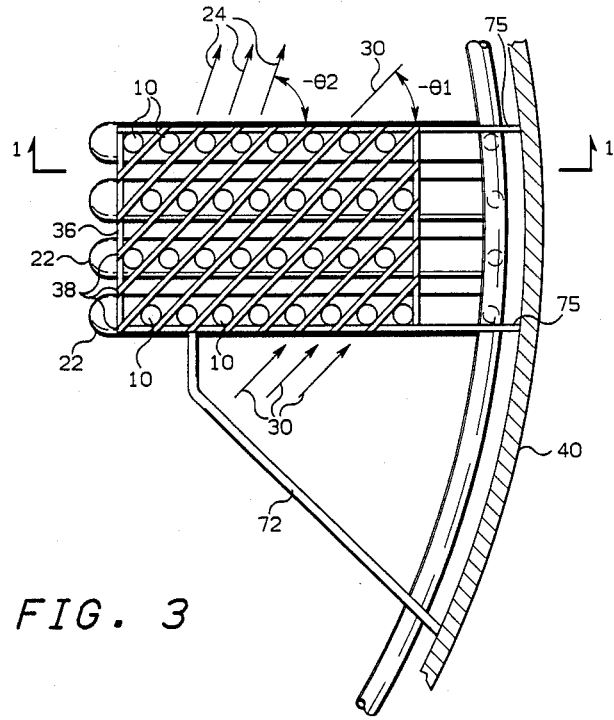
FIGS. 2 and 3 are cross-sectional views of the device of FIG. 1 as would be seen when looking along the indicated lines.
Figure 2:
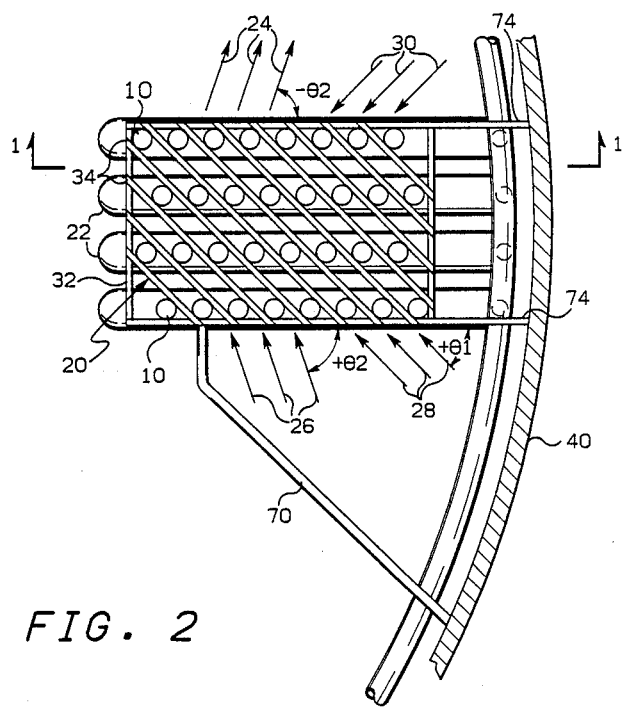

FIG. 1 shows a plurality of parallel tubes 10 forming a tube bundle 20 having a longitudinal axis which is parallel to the tubes 10. With reference to FIGS. 2 and 3, the tubes 10 are arranged in a plurality of parallel tube rows 22. Regular straight lanes 24, 26, 28, and 30 are defined through the tube bundle transverse to the direction of the tube row 22. The tubes are laid out so there is a first plurality of lanes 28 being defined through the tube bundle at an angle of about $+\theta 1$ with respect to the direction of the tube rows 22 and a second plurality of lanes 30 being defined through the tube bundle at an angle of $-\theta 1$ with respect to the direction of the tube rows 22. There is also a third plurality of lanes 26 defined by the tubes in the tube bundle which are at an angle of $+\theta 2$ with respect to the tube rows 22 and a fourth plurality of lanes 24 defined through the tube bundle at an angle of $-\theta 2$ with respect to the direction of the tube rows 22. $\theta 1$ ranges from about 10° to about 60°. $\theta 2$ ranges from about 40° to about 80°. $\theta 2$ is also greater than $\theta 1$.

In accordance with an embodiment of the invention, the tubes of the bundle are supported by rod baffles wherein the rod baffles are formed from a band or ring and a plurality of rods attached to the band. With reference to FIG. 2, a first band 32 embraces an outer tube limit of the tube bundle 20. A first plurality of rods 34 is attached to the first band 32 and extends through the first plurality of lanes 28. The rods of the first plurality of rods are of sufficient diameter to contact the tubes 10 defining the limits of each lane of the first plurality 28 of lanes and each tube 10 of the tube bundle 20 is contacted by at least one rod 34 of the first plurality of rods. With reference to FIG. 3, a second band 36, is spaced longitudinally apart from the first band 32 with respect to the longitudinal axis of the tube bundle 20 (see FIG. 1) and embraces the outer tube limits of the tube bundle. A second plurality of rods 38 is attached to the second band 36 and extends through the second plurality of lanes 30. Each rod 38 of the second plurality of rods is also of sufficient diameter to contact the tubes defining the limits of each lane of the second plurality 30 of lanes. Each tube 10 of the bundle 20 is contacted by at least one rod of the second plurality of rods.

It is preferred in the practice of the invention that the tube bundle 20 be further characterized by the absence of rods extending along the third plurality of lanes 24 and the fourth plurality of lanes 26. By providing complimentary rods that are set at an angle of near 90° with respect to each other the structural rigidity of the tube bundle can be enhanced. It is thus preferred that the angle between the first plurality of lanes and the second plurality of lanes in which the rods are positioned range from about 60° up to about 120°.

The spacing between the tubes can be described in terms of the outer diameter D of the tubes 10 of the bundle 20. Generally speaking, a distance of at least 2 D will separate the tube rows 22 as measured tube center to tube center. Usually, the distance between the adjacent tube rows 22 will range from about 2 D to about 4 D. Adjacent tubes in the same row will usually be separated by a distance in the range of from about 1.5 D to about 2.5 D, as measured center to center. The distance separating the tube rows will generally be greater than the distance separating adjacent tubes in the same row. It is further preferred in the construction of the tube bundle of the invention that the tubes be laid out in a triangular pitch, so that fluid flowing transversely through the tube bundle will tend to flow over the tubes rather than channeling through the lanes, resulting in poor heat exchange.

Referring back to FIG. 1, each row 22 of tubes is connected to an inlet header 3 and an outlet header 7. The inlet header 3 can be positioned beneath the opposite end of the tube rows than the inlet header if desired, for clearance for example. A fluid inlet 1 extends through a sidewall 40 of a vessel to provide fluid to the inlet header 3. A fluid outlet port 11 extends through the vessel wall 40 to provide for withdrawal of fluid from the outlet header 7 from the vessel. Riser pipes 42 connect the inlet header 3 with a split pipe header 5 upon which the row 22 of tubes 10 is mounted. Riser pipe 44 connects the split pipe header 45 with the outlet header 7.

Figure 4:
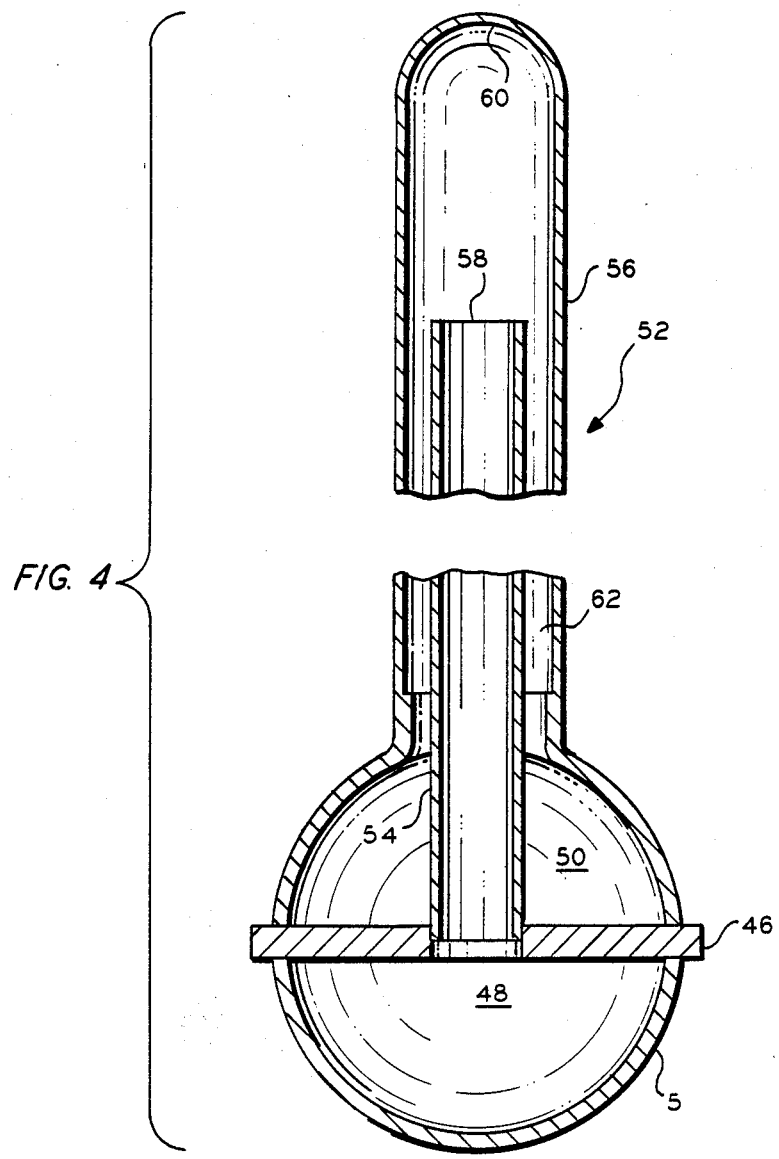
FIG. 4 is a cross-sectional view of a portion of the tube bundle as would be seen in FIG. 1 when viewed along the indicated lines.
Figure 5:
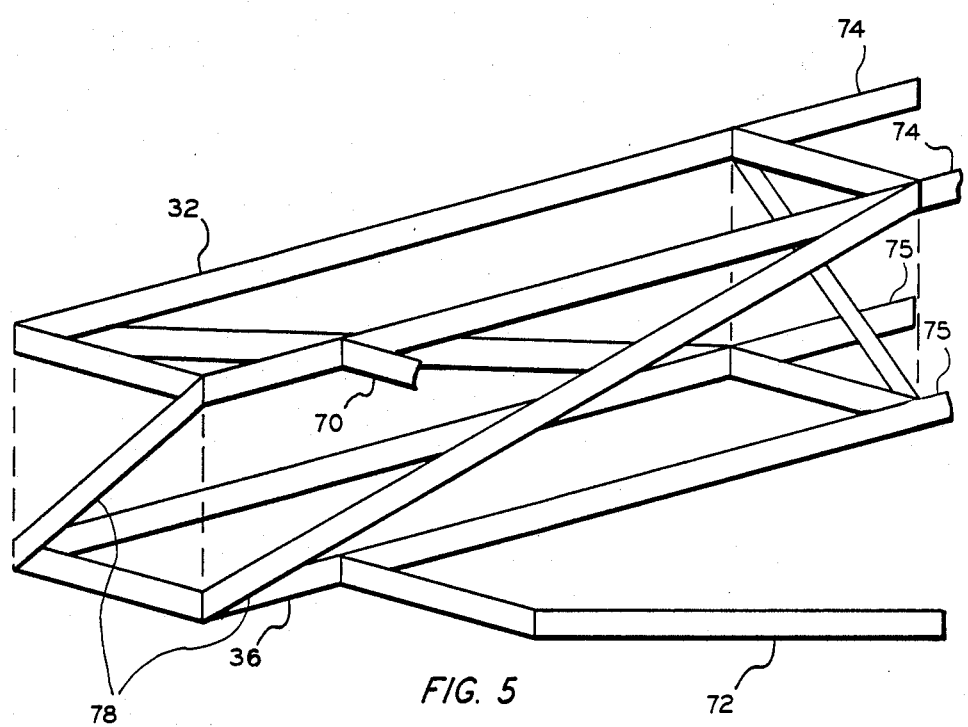
FIG. 5 is a pictorial representation of a portion of the apparatus shown in FIG. 1.

With reference to FIG. 4, a partition plate 46 divides the split pipe header 5 into an inlet chamber 48 and an outlet chamber 50. The riser pipes 42 connect the inlet chamber 48 with the inlet header 3. In a preferred embodiment of the invention, the tubes 10 each comprise a bayonet tube assembly 52 which is attached to the split pipe header 5. The tube assembly 52 comprises a first inner tube 54 (the bayonet) and a second, outer tube 56 (the sheath) concentrically positioned around the inner tube 54. A first end of the inner tube 54 is mounted to a passage through the plate 46. A second end 58 of the inner tube 54 is spaced apart from an endcap 60 on the outer tube 56. The outer tube 56 is mounted to a port through the sidewall of the split pipe header 5 thus forming a flow path from the inlet chamber 48 through the inner tube 54 to the second end of the bayonet tube assembly 52 and from the second end of the bayonet tube assembly through an annulus 62 defined between the inner tube 54 and the outer tube 56 to the outlet chamber 50 of the split pipe header 5. From the outlet chamber 50, the fluid flows up riser 44 to outlet header 7 and is withdrawn from the apparatus at port 11.

The tube bundle of the invention is preferably employed for a process involving exchanging heat with the fluid in a stirred vessel. The fluid in the stirred vessel is flowed through the tube bundle and passes between the tubes in the parallel rows of parallel tubes. The vessel is preferably stirred by a stirrer 64 positioned along the axis of the shell 66. See FIG. 6. A plurality of tube bundles are preferably positioned around the inside surface of the shell between the longitudinal axis of the shell and an inside surface of the shell. The tube rows are preferably lined up along chords extending across a generally cylindrical portion of the sidewall of the vessel. The inside diameter of the shell should be at least 2.5 times the length of the tube rows and is preferably in the range of 2.5 to 5 times the length of said tube rows. Generally, from about 2 to about 20 rows of tubes form each tube bundle and the tubes in adjacent rows are displaced so that the tubes are laid out in a triangular pitch. Preferably, each tube bundle is formed from about 3 to about 12 rows of tubes. The individual tubes are provided with radial support by a pair of rod baffles such as hereinabove described wherein each baffle contains sufficient rods so that each tube in the tube bundle is supported on two sides by each rod baffle and the pair of rod baffles together support all four sides of each tube thereby providing the radial support.

In a preferred embodiment of the invention a first strut 70 extends transversely from the tube bundle 20 with respect to the rows 22 of tubes and connects the first band 32 with an inside surface of the shell 40. See FIG. 2. A second strut 72 similarly extends from the tube bundle 20 transversely with respect to the tube rows 22 and connects the second band 36 with an inside surface of the shell 40. See FIG. 3. Additional struts 74 and/or 75 connect at least one of the first band 32 or the second band 36 with the inside surface of the shell. The struts 74 and 75 extend from the tube bundle 20 generally parallel to the direction of the tube rows 22. To provide the tube bundle 20 with greater rigidity, a plurality of braces 78 can be provided to connect the first band 32 with the second band 36. In a preferred emnbodiment, the braces follow a co-rotational path which extends around a first circumferential portion of the tube bundle thereby providing the bundle with greater resistance to twisting.

Where the tube bundle is to be used in a fermentor for the production of yeast or bacteria it is desirable that construction be sufficiently open to facilitate thorough cleaning between runs. Wide spacing between the individual tubes of the tube bundle is thus desirable. To support the widely spaced tubes requires relatively large sized support rods. It can also be desirable to position the rods at highly oblique angles through the tube bundle so that the increased rod diameter brought on by the greater spacing between the tube rows is minimized. Generally speaking, where the spacing between adjacent tubes in the same row is in the range of from about 1.5 D to about 2.5 D, D being the outside diameter of the tubes, the spacing between adjacent rows of tubes is in the range of from about 2 D to about 4 D and the rods have a diameter in the range of from about 0.5 D to about D.

Figure 6:
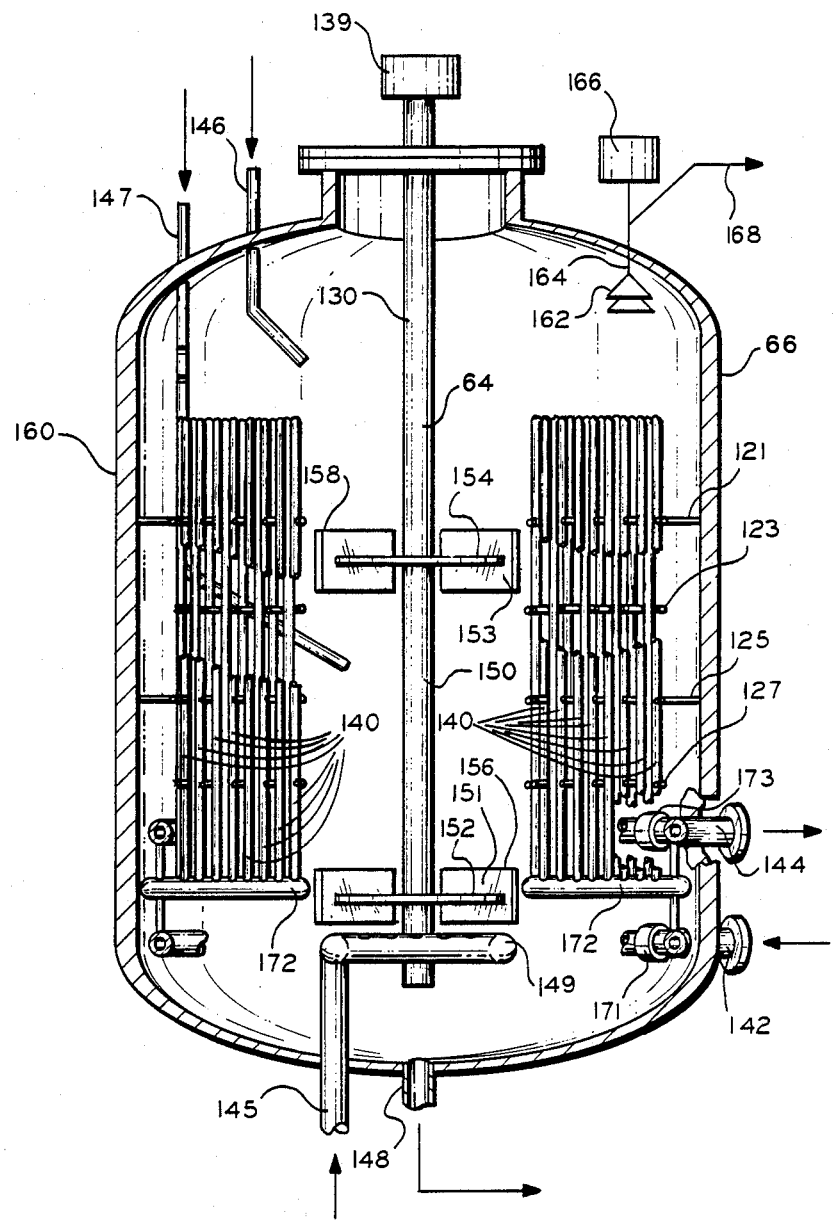
FIG. 6 is a pictorial representation, taken in partial cross-section and with parts of the device broken away, illustrating certain features of the invention as would be employed in a particularly preferred embodiment.

FIG. 6 illustrates a preferred embodiment of the invention as employed in a fermentor.

Vessel 160, as illustrated in FIG. 6, is equipped with shaft 130 which is driven by drive means 139. Shaft 130 is shown fitted with two impellers, 156 and 158. Impellers 156 and 158 are constructed of disc 152 and 154, respectively, on which a plurality of blades 151 and 153, respectively, are mounted. Those of skill in the art recognize that a greater number of impellers can be employed, depending on vessel height, width, the dimensions of the heat exchange means, etc. As shown in FIG. 6, it is preferred that the bottom-most impeller be positioned in close proximity to sparger 149, to facilitate oxygen transfer in the fermentation fluid. By the term "close proximity", it is meant that the bottom-most impeller and the sparger are positioned with about ⅛ to 1/10 impeller diameters from one another.

Additional impellers can be employed on shaft 130 in a variety of relative orientations. For ease of mounting on stirring shaft 130, multiple impellers can be spaced equally along the shaft, with the uppermost impeller being preferably positioned at about 60 percent of the vessel height, as shown in FIG. 6 for impeller 158.

The general dimensions of vessel 160 are preferably selected such that the ratio of length to diameter is generally in the range of about 0.1 up to 10:1. Preferably, the ratio of length to diameter is in the range of about 0.3 up to 5:1, with the ratio of length to diameter most preferably falling in the range of about 1 up to 4:1 for fermentation service.

Heat exchange fluid is provided to parallel tubes 140 via inlet means 142, as shown in FIG. 6. Heat exchange fluid passing through inlet 142 is distributed through pipe 171 to headers 172 and into tubes 140. After heat exchange fluid passes through tube 140, it is collected from headers 172 via pipe 173 and discharged via outlet means 144. At least two baffles, each comprising a first inlet and a first outlet means (reference numerals 142 and 144 respectively) and parallel tubes 140, are employed in the invention vessel. As illustrated in FIG. 6, each baffle comprises a bundle of parallel tube rows. The tubes 140 in each baffle are typically about 25–90% of the length of the straight portion of the vessel, not including the domed vessel heads.

A widely varied number of tube bundles can be employed, depending on the size of the tube bundles, the number of tubes per bundle, etc. Up to as many as 30 bundles per vessel can be employed, within the range of about 4 up to 24 baffles per vessel being preferred.

As one alternative, the tube bundles can be assembled as a stacked array of a plurality of bundles, each of which is shorter than the total length of tube bundles assembled in the fermentor vessel. By assembling the bundles as a stacked array of short segments, with a total length equivalent to the 25–90% of total straight vessel length, shorter tubestubes which are more resistant to vibration and thermal stresses during the conversion process carried out in the vessel can be used. Up to about 10 tube bundle assemblies, which, in total, occupy about 25–90% of the straight vessel length of the fermentor vessel, can be stacked to provide the required heating and cooling capacity.

The blades 151 can be mounted on the disc 152 in a variety of ways, e.g., with blades 151 mounted both perpendicular to the plane of the disc and on a radial projection from the vertical axis of the disc, or, alternatively, the blades 151 can be mounted on the disc 152 oriented at some angle with respect to the axis of the disc. Alternatively, impeller designs other than the specific design illustrated herein, can be employed, such as, for example, axial flow impellers, marine type propellers, and the like.

The upper limit as to impeller diameter is defined by the inner diameter of the tube bundles forming heat exchange means for the fermentor. An impeller diameter which approaches this upper limit will provide the maximum amount of mixing per impeller. It is preferred that the impeller diameter not be smaller than about 10% of the total internal vessel diameter, and generally the impeller diameter will not exceed about 50% of the total internal vessel diameter. Preferably, an impeller diameter of about 20% to 35% of the total internal vessel diameter will be employed.

As shown in FIG. 6, fermentation vessel 160 is also provided with first inlet 146 and second inlet 147, as well as gas inlet 145. While vessel 160 is illustrated with the two inlets 146 and 147, all feed to the fermentor could be introduced via only one inlet means or a plurality of inlet means, wherein various feed components are separately introduced. For example, for many fermentation processes, it is desirable to introduce the nutrient media and the carbon and energy source as separate feed streams, so vessel 160 is shown in FIG. 6 as a preferred embodiment equipped with the two separate inlet means 146 and 147. While inlets 146 and 147 are illustrated with one discharge port each, more dispersed introduction of feed can be achieved by employing inlets having multiple discharge ports. In addition, the inlet ports can be conveniently located at various positions about the fermentation vessel, frequently being positioned as dictated by considerations of engineering expediency.

Inlet 145 is used to introduce oxygen and optionally the nitrogen source to the fermentation vessel. Gas introduced via inlet 145 enters the fermentation vessel through sparger 149. The sparger is positioned symmetrically in the fermentor vessel with respect to the longitudinal axis of fermentor vessel and has a face side containing a plurality of holes therein. the diameter of the sparging means is preferably no greater than the diameter of the bottom-most impeller under which the face side of the sparger is preferably closely positioned.

The method of gas introduction, plus the location of impeller 156 in close proximity to sparger 149, as well as the position of the tube bundles, all contribute to the extremely high level of oxygen transfer of which the inventive fermentation apparatus is capable. The fermentation vessel of the invention is capable of oxygen transfer rates in the range of at least about 300 millimoles of oxygen per liter per hour (mmol $O_2$/L/hr). In addition, the heat removal capability of the invention fermentation vessel is sufficient to remove the large amounts of heat produced by the fermentation, which large amounts of heat are generated as a result of the high levels of oxygen made available to the fermentation broth. Thus, heat removal on the order of at least about 36 Kcal/liter/hour are possible with fermentation apparatus constructed in accordance with the present invention.

Fermentation vessel 160 is also equipped with means for removing ferment, i.e. port 148. When fermentation is carried out in continuous mode, continuous or intermittent withdrawal of ferment can be accomplished via port 148 while fresh nutrients are provided via inlets 146, 147 and 145.

Fermentation vessel 160 is further preferably equipped with at least one means for degassing foam, e.g., a foam breaker, such as for example the foam breaker disclosed by Hunt in U.S. Pat. No. 4,373,024, assigned to Phillips Petroleum Company, or the assembly of elements 162, 164 and 166 illustrated in FIG. 6. Cones 162 are mounted on shaft 164 which is rotated by drive means 166. The impact of foaming ferment with rotating cones 162 causes disruption of the foam and causes liquid to return to the main part of the fermentation vessel while gas released from the foam exits the fermentor via line 168. While at least one foam breaker will be employed on the invention fermentation vessel, sufficient foam breaking capacity to handle the amount of foam anticipated from a given fermentation process can be provided by an appropriate number of foam breakers located about the dome portion of the fermentation vessel.

The aqueous aerobic fermentation process requires molecular oxygen which is supplied by a molecular oxygen-containing gas such as air, oxygen-enriched air, or even substantially pure molecular oxygen, so as to maintain the ferment with an oxygen partial pressure effective to assist the microorganism species in growing or in biochemically converting substrate in a thriving fashion. By using an oxygenated hydrocarbon substrate, the total oxygen requirements for growth or substrate conversion of the microorganism can be reduced from the requirements when a paraffin is used.

The pressure employed for the microbial fermentation step can range widely. Typical pressures are in the range of about 0 to 150 psig, presently preferably about 0 to 60 psig, more preferably 35 to 40 psig, as a balance of equipment and operating costs versus oxygen solubility achieved. Greater than atmospheric pressure are advantageous in that such pressures do tend to increase the dissolved oxygen concentration in the aqueous ferment, which in turn can help increase cellular growth rates. At the same time this is counterbalanced by the fact that high pressures do increase equipment and operating costs.

Reasonable variations from and modifications of this invention as disclosed herein are contemplated to be within the scope of patent protection desired and sought.

That which is claimed is:

1. Apparatus comprising:
    (a) a plurality of parallel tubes forming a tube bundle having a longitudinal axis, such tubes being arranged in a plurality of parallel tube rows with regular straight lanes being defined through the tube bundle transverse to the direction of the tube rows, there being a first plurality of lanes defined through the tube bundle at an angle of $+\theta 1$ with respect to the direction of the tube rows and a second plurality of lanes being defined through the tube bundle at an angle of $-\theta 1$ with respect to the direction of the tube rows, there being a third plurality of lanes defined through the tube bundle at an angle of $+\theta 2$ with respect to the direction of the tube rows and a fourth plurality of lanes defined through the tube bundle at an angle of $-\theta 2$ with respect to the direction of the tube rows, wherein $\theta 1$ is in the range of 10° to 60° wherein $\theta 2$ is in the range of 40° to 80°, and wherein $\theta 2$ is greater than $\theta 1$,
    (b) a first band embracing an outer tube limit of the tube bundle,
    (c) a first plurality of rods attached to said first band and extending through the first plurality of lanes, each rod of said first plurality of rods being of sufficient diameter to contact the tubes defining the limits of each lane of the first plurality of lanes, each tube of the tube bundle being contacted by at least one rod of the first plurality of rods,
    (d) a second band spaced longitudinally apart from the first band with respect to the longitudinal axis of the tube bundle, said second band embracing the outer tube limit of the tube bundle; and
    (e) a second plurality of rods attached to said second band extending through said second plurality of lanes, each rod of said second plurality of rods being of sufficient diameter to contact the tubes defining the limits of each lane of the second plurality of lanes, each tube of the tube bundle being contacted by at least one rod of the second plurality of rods.

2. Apparatus as in claim 1 wherein said tube bundle is further characterized by the absence of rods extending along the third plurality of lanes and the fourth plurality of lanes.

3. Apparatus as in claim 2 wherein the tubes have an outer diameter D; and wherein a distance of at least 2 D separates the tube rows, as measured tube center to tube center.

4. Apparatus as in claim 3 wherein a distance in the range of 2 D to 4 D separates adjacent tube rows, and a distance in the range of 1.5 D to 2.5 D separates adjacent tubes in the same tube row, as measured tube center to tube center, and wherein the distance separating tube rows is greater than the distance separating adjacent tubes in the same row.

5. Apparatus as in claim 4 wherein the tubes are laid out in a triangular pitch.

6. Apparatus as in claim 5 further comprising a shell surrounding the tube bundle, said shell having a longitudinal axis parallel to and spaced apart from the longitudinal axis of the tube bundle, said tube bundle being positioned in the shell between the longitudinal axis of the shell and an inside surface of the shell.

7. Apparatus as in claim 6 wherein the shell has a generally cylindrical inside surface, the tube rows are positioned along chords across generally cylindrical inside surface of the shell, and the inside diameter of the shell is at least 2.5 times the length of the tube rows.

8. Apparatus as in claim 7 wherein the inside diameter of the shell is in the range of 2.5 to 5 times the length of the tube rows, said apparatus further comprising a plurality of tube bundles circumferentially positioned around the inside surface of the shell and a stirrer positioned along the axis of the shell to cause fluid flow transversely through the plurality of tube bundles.

9. Apparatus as in claim 8 further comprising a first strut extending from the tube bundle transversely with respect to the tube rows connecting the first band with the generally cylindrical inside surface of the shell and a second strut extending from the tube bundle transversely with respect to the tube rows connecting the second band with the generally cylindrical inside surface of the shell.

10. Apparatus as in claim 9 further comprising a plurality of braces connecting the first band with the second band, said plurality of braces following a co-rotational path around a portion of the tube bundle.

11. Apparatus as in claim 10 further comprising an inlet header connected to each row of tubes and an outlet header connected to each row of tubes.

12. Apparatus as in claim 11 wherein each tube bundle comprises in the range of from 3 to 10 rows of tubes.

* * * * *